United States Patent
US 10,918,586 B2
Horn
(45) Date of Patent: Feb. 16, 2021

(12) United States Patent
(10) Patent No.: US 10,918,586 B2
Horn
(45) Date of Patent: Feb. 16, 2021

(54) TOPICAL COMPOSITIONS AND METHODS OF USE THEREOF

(71) Applicant: PS Therapy Ltd, Bridgetown (BB)

(72) Inventor: Gerald Horn, Deerfield, IL (US)

(73) Assignee: PS Therapy Ltd., Bridgetown (BB)

( * ) Notice: Subject to any disclaimer, the term of this patent is extended or adjusted under 35 U.S.C. 154(b) by 0 days.

(21) Appl. No.: 16/208,646

(22) Filed: Dec. 4, 2018

(65) Prior Publication Data

US 2019/0175481 A1 Jun. 13, 2019

Related U.S. Application Data

(60) Provisional application No. 62/595,656, filed on Dec. 7, 2017.

(51) Int. Cl.

| A61K 8/66 | (2006.01) |
|---|---|
| A61Q 19/08 | (2006.01) |
| A61K 8/49 | (2006.01) |
| A61K 8/20 | (2006.01) |
| A61K 8/92 | (2006.01) |
| A61K 8/73 | (2006.01) |
| A61K 8/34 | (2006.01) |
| A61K 8/84 | (2006.01) |
| A61K 38/48 | (2006.01) |
| A61K 31/00 | (2006.01) |
| A61K 8/38 | (2006.01) |
| A61P 17/10 | (2006.01) |
| A61K 8/39 | (2006.01) |
| A61K 31/60 | (2006.01) |
| A61K 8/368 | (2006.01) |
| A61K 8/86 | (2006.01) |
| A61K 8/64 | (2006.01) |
| A61Q 19/00 | (2006.01) |
| A61K 31/327 | (2006.01) |

(52) U.S. Cl.
CPC .............. *A61K 8/66* (2013.01); *A61K 8/20* (2013.01); *A61K 8/345* (2013.01); *A61K 8/368* (2013.01); *A61K 8/38* (2013.01); *A61K 8/39* (2013.01); *A61K 8/4973* (2013.01); *A61K 8/64* (2013.01); *A61K 8/731* (2013.01); *A61K 8/738* (2013.01); *A61K 8/84* (2013.01); *A61K 8/86* (2013.01); *A61K 8/922* (2013.01); *A61K 31/00* (2013.01); *A61K 31/327* (2013.01); *A61K 31/60* (2013.01); *A61K 38/4893* (2013.01); *A61P 17/10* (2018.01); *A61Q 19/00* (2013.01); *A61Q 19/08* (2013.01); *C12Y 304/24069* (2013.01)

(58) Field of Classification Search
CPC .......... A61K 8/66; A61K 8/4973; A61K 8/20; A61K 8/922; A61K 8/738; A61K 8/731; A61K 8/345; A61K 8/84; A61Q 19/08
See application file for complete search history.

(56) References Cited

U.S. PATENT DOCUMENTS

| 7,727,537 B2* | 6/2010 | Modi ................... A61K 8/0291 424/239.1 |
| 8,404,249 B2* | 3/2013 | Dake ........................ A61P 5/14 424/247.1 |
| 2010/0150984 A1* | 6/2010 | Kennedy ................. A61F 2/022 424/424 |
| 2011/0106021 A1 | 5/2011 | Ruegg et al. |
| 2015/0297723 A1* | 10/2015 | Kisak ................... A61K 31/245 514/179 |
| 2016/0250302 A1 | 9/2016 | Ruegg et al. |
| 2017/0041983 A1* | 2/2017 | Jha ........................ H04W 76/28 |

OTHER PUBLICATIONS

"Pharmaceutical Calculations" (Internet article (2015), 16 Pages: Retrieved from https://clinicalgate.com/pharmaceutical-calculations/ (Year: 2015).*
International Preliminary Report on Patentability, dated Jun. 9, 2020, issued in corresponding PCT Application No. PCT/US2018/063816.

* cited by examiner

*Primary Examiner* — Sean C. Barron

(74) *Attorney, Agent, or Firm* — Wood, Phillips, Katz, Clark & Mortimer

(57) ABSTRACT

The present invention is directed to topical compositions containing botulinum toxin, benzoyl peroxide, salicylic acid or a mixture of benzoyl peroxide and salicylic acid. The present invention is further directed to methods of treating acne or reducing rhytides with these topical compositions.

8 Claims, 1 Drawing Sheet
(1 of 1 Drawing Sheet(s) Filed in Color)

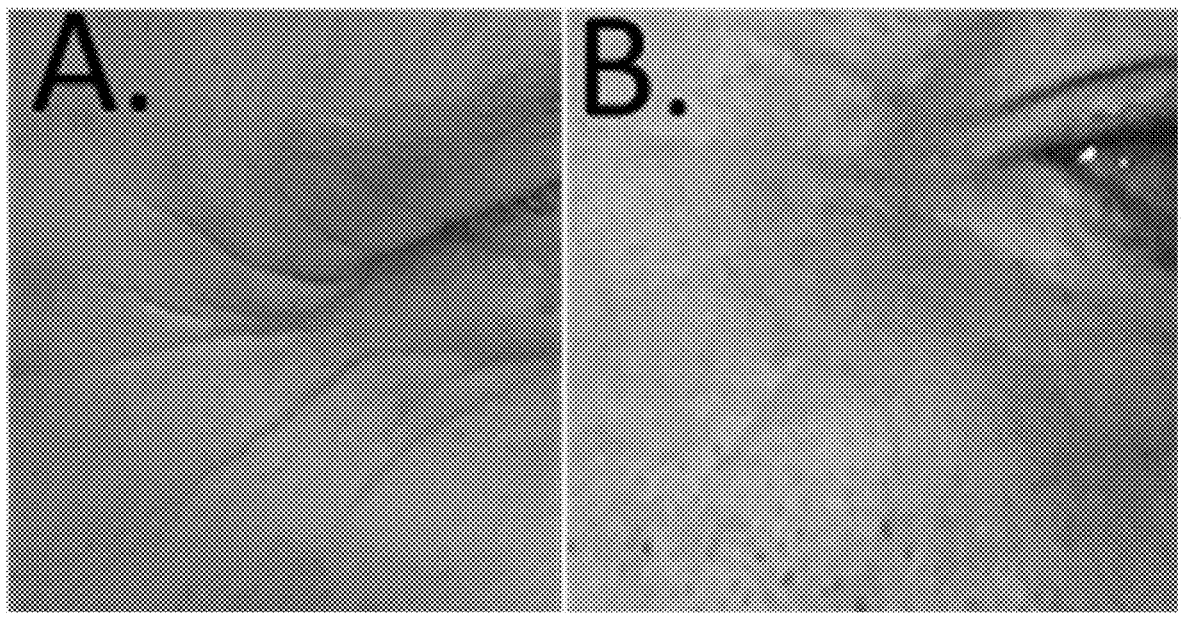

TOPICAL COMPOSITIONS AND METHODS OF USE THEREOF

FIELD OF THE INVENTION

The present invention is directed to topical compositions containing botulinum toxin, benzoyl peroxide, salicylic acid or a mixture of benzoyl peroxide and salicylic acid. The present invention is further directed to methods of treating acne or reducing rhytides with these topical compositions.

BACKGROUND OF THE INVENTION

In contemporary culture both men and women are expected to maintain a wrinkle free appearance for as long as possible. Due to external pressure to maintain a youthful appearance many adults in their thirties and beyond undergo medical procedures to do so. However, the cost of these elective medical procedures can be more than many individuals can afford and are often not covered by medical insurance. Alternatives to medical procedures have been advanced in recent years including the injection of the botulinum toxin.

To achieve a wrinkle free appearance botulinum toxin is injected in the affected areas. The botulinum toxin works by temporarily paralyzing the underlying musculature and thus preventing the appearance of wrinkles caused by the excitation and contraction of these muscles. These injections must be done on a regular basis and the need to have physician administered injections is burdensome.

Alternatives to injection include "aging" creams. These creams are applied topically and are much easier and less burdensome to the person applying them. However, these creams do not prevent the appearance of wrinkles. Thus, there is a need in the art for a topical botulinum toxin topical composition that effectively delivers the agent to the underlying musculature and prevents or reduces the appearance of wrinkles.

On the other end of the aging spectrum, acne is a major concern among teenagers and twenty-somethings and even some individuals in their thirties and older. Acne is a common inflammatory disease of the skin, mainly on the face and back. While various topical treatment for acne exist not everyone is able to benefit. Some individuals continue to have problems treating their acne despite utilizing the readily available treatments including benzoyl peroxide and salicylic acid. A potential cause of the ineffectiveness of these treatments is the lack of delivery through the outer layers of the skin. Thus, there is a need in the art for a topical acne treatment composition that can deliver the active agent to the desired tissue and effectively treat acne.

SUMMARY OF THE INVENTION

The present invention is directed to topical compositions comprising botulinum toxin, one or more nonionic surfactants and at least one excipient selected from one or more viscosity enhancers, a polyol and one or more electrolytes.

The present invention is further directed to topical compositions comprising an active ingredient comprising benzoyl peroxide, salicylic acid or a mixture thereof, one or more nonionic surfactants and at least one excipient selected from one or more viscosity enhancers, a polyol, benzyl alcohol and glycofurol.

The present invention is further directed to a method of treating rhytides comprising topically applying a botulinum toxin composition of the present invention to a subject in need thereof.

The present invention is further directed to a method of treating acne comprising topically applying a benzoyl peroxide and/or salicylic acid composition of the present invention to a subject in need thereof

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Reduction in rhytides following topical application of botulinum composition #B1. Panel A shows rhytides prior to application and Panel B shows reduced rhytides following application.

DETAILED DESCRIPTION OF THE INVENTION

The Applicant has unexpectedly developed a topical botulinum toxin composition that is effective in treating rhytides. Further, the Applicant has developed an improved acne treatment composition.

As used herein, the term "composition" is intended to encompass a product comprising the specified ingredients in the specified amounts, as well as any product which results, directly or indirectly, from a combination of the specified ingredients in the specified amounts.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

Throughout the application, the singular forms "a," "an," and "the" include plural reference unless the context clearly dictates otherwise.

As used herein the term "polyol" refers to compounds with multiple hydroxyl functional groups available for organic reactions such as monomeric polyols such as glycerin, pentaerythritol, ethylene glycol and sucrose. Further, polyols may refer to polymeric polyols including glycerin, pentaerythritol, ethylene glycol and sucrose reacted with propylene oxide or ethylene oxide.

As used herein, "acne" refers to Acne vulgaris and related conditions.

As used herein, "rhytides" refers to a fold, ridge or crease in the skin and includes, but is not limited to, rhytides caused by aging, sleeping position and/or loss of body mass.

As used herein the term "treatment" or "treating" refers to preventing, ameliorating, reducing or abolishing a disease, disorder or condition or symptoms of a disease, disorder or condition.

The present invention is directed to topical compositions comprising botulinum toxin, one or more nonionic surfactants and at least one excipient selected from one or more viscosity enhancers, a polyol and one or more electrolytes.

The present invention is further directed to topical compositions comprising botulinum toxin, polysorbate 80, poloxamer 407, poloxamer 188, polyoxyl castor oil, hydroxypropyl-gamma-cyclodextrin, hydroxypropylmethyl cellulose, mannitol, magnesium chloride, sodium chloride and sorbate and optionally, menthol, benzalkonium chloride and/or disodium ethylenediaminetetraacetic acid.

The present invention is further directed to topical compositions comprising an active ingredient comprising or consisting of benzoyl peroxide, salicylic acid or a mixture thereof, one or more nonionic surfactants and at least one excipient selected from one or more viscosity enhancers, benzyl alcohol and glycofurol.

The present invention is further directed to topical compositions comprising an active ingredient consisting of benzoyl peroxide, salicylic acid or a mixture thereof, polysorbate 80, poloxamer 407, poloxamer 188, polyoxyl castor oil, hydroxypropylmethyl cellulose, sorbate, benzyl alcohol and glycofurol and optionally, menthol, benzalkonium chloride and/or disodium ethylenediaminetetraacetic acid.

The present invention is further directed to a method of treating rhytides comprising topically applying a botulinum toxin composition of the present invention to a person in need thereof.

The present invention is further directed to a method of treating acne comprising topically applying a benzoyl peroxide and/or salicylic acid composition of the present invention to a person in need thereof.

Botulinum toxin, as used herein, refers to the proteinaceous toxins produced by *Clostridium botulinum* composing a heavy chain with a molecular weight of about 100 kiloDaltons and a light chain with a molecular weight of about 50 kiloDaltons. Botulinum toxin has seven serotypes referred to as A, B, C, D, E, F and G. Serotype A is commercially available under the tradename Botox® (Botox is available from and a trademark of Allergan, Inc.). In a preferred embodiment botulinum toxin is present in compositions of the present invention at an amount from about 1 unit to about 1,000 units, more preferably from about 10 to about 500 units, yet more preferably from about 50 to about 200 units and most preferably about 100 units. 1 unit of botulinum toxin is the amount of toxin necessary to kill, upon injection, 50% of a group of Swiss Webster mice weighing from 18 to 20 grams each.

Benzoyl peroxide is present in compositions of the present invention at a concentration from about 2.5% to about 10% w/v, more preferably from about 2.5% to about 7.5% w/v and most preferably about 2.5%, 5.0% or 7.5% w/v.

Salicylic acid is present in the compositions of the present invention at a concentration from about 0.5% to about 2.0% w/v, more preferably from about 0.5% to about 1.5% w/v and most preferably about 0.5%, 1.0% or 1.5% w/v.

Benzyl alcohol is present in the compositions of the present invention at a concentration from about 1.0% to about 2.0% w/v.

Glycofurol is present in the compositions of the present invention at a concentration from about 1.0% to about 20.0% w/v, preferably from about 1% to about 10% w/v and more preferably from about 1% to about 5% w/v.

Nonionic surfactants suitable for use in the present invention include, but are not limited to, poloxamers, polysorbates, cyclodextrins, alkylaryl polyethers, polyoxyethyleneglycol alkyl ethers, tyloxapol, and polyoxyls. Poloxamers are nonionic triblock copolymers composed of a central hydrophobic chain of polyoxypropylene (poly(propylene oxide)) flanked by two hydrophilic chains of polyoxyethylene (poly(ethylene oxide)). Polysorbates are oily liquids derived from ethoxylated sorbitan esterified with fatty acids. Cyclodextrins are composed of 5 or more α-D-glucopyranoside units linked together at position 1 and 4. Polyoxyls are a mixture of mono- and diesters of stearate and polyoxyethylene diols. Preferred embodiments include but are not limited to poloxamers-poloxamer 188 and poloxamer 407; polysorbates-polysorbate 20, polysorbate 60, polysorbate 80, tyloxapol, Brij® 35, Brij® 78, Brij® 98 and Brij® 700, Span® 20, Span® 40, Span® 60, Span® 80; cyclodextrins-2-HP-cyclodextrin, ionically charged (e.g. anionic) beta-cyclodextrins with or without a butyrated salt (Captisol®); (sulfobutylether β-cyclodextrin, Captisol is a registered trademark of Cydex Pharmaceuticals), hydroxypropyl-gamma-cyclodextrin, gamma cyclodextrin; and polyoxyls-polyoxyl 40 stearate, polyoxyl 30 castor oil, polyoxyl 35 castor oil, and polyoxyl 40 hydrogenated castor oil; or combinations thereof. Polyols are not included in the term "nonionic surfactants." Total nonionic surfactant concentrations of the present invention are from about 1.25% to about 7.0% w/v, preferably, 1.5% to about 7.0% w/v, more preferably from about 3.0% to about 7.0% w/v, yet more preferably from about 3.5% to about 6.7% w/v and most preferably about 3.65% or about 6.7% w/v.

In preferred embodiments, the one or more nonionic surfactants include a polysorbate, such as polysorbate 80.

In more preferred embodiments the amount of polysorbate is from about 0.01% to about 4.0% w/v, preferably from about 0.5% to about 3.5% w/v, preferably about 0.5%, 1.0%, 1.5%, 2.0%, 2.5%, 2.75%, 3.0% and 3.5% w/v.

In other preferred embodiments, the one or more nonionic surfactants include a poloxamer such as poloxamer 188 and or poloxamer 407, a polyoxyl such as a polyoxyl castor oil including polyoxyl 35 castor oil or polyoxyl 40 hydrogenated castor oil, and a cyclodextrin, such as hydroxypropyl-gamma-cyclodextrin.

In other more preferred embodiments the one or more nonionic surfactants comprises from about 0.01% to about 3.0% w/v of poloxamer 407, preferably, from about 0.2% to about 0.5% w/v, preferably, about 0.1%, 0.2%, 0.5%, 0.7%, 1.0% and 5.0% w/v.

In other more preferred the one or more nonionic surfactants comprises from about 0.01% to about 3.0% w/v of poloxamer 188, preferably from about 0.1% w/v to about 1.5% w/v, more preferably from about 1.0% to about 1.5% w/v and most preferably about 1.0% or 1.5% w/v.

In other more preferred the one or more nonionic surfactants comprises from about 0.001% to about 2.0% w/v of polyoxyl castor oil, preferably, from about 0.005% to about 1.0% w/v, more preferably, from about 0.015% to about 0.5% w/v and most preferably 0.015% or 0.5% w/v.

In other more preferred the one or more nonionic surfactants comprises from about 0.01% to about 5% w/v of hydroxypropyl-gamma-cyclodextrin, preferably from about 0.5% to about 5% w/v, more preferably, from about 1.5% to about 3.0% w/v, and most preferably, about 0.25%, 0.5%, 0.7%, 0.75%, 1.0%, 1.5%, 2.0%, 2.5%, 3.0%, 3.5%, 4.0% and 5.0% w/v.

Viscosity enhancers suitable for use in the present invention are non-Newtonian viscosity enhancers, which include, but are not limited to cellulose derivatives, carbomers (Carbopol®), gums, and hyaluronic acids (hyaluronates), dextrans, polyvinyl alcohol, polyacrylic acids, povidone, polyethylene glycol, propylene glycol and chitosans; where for cellulose derivatives particularly preferred are one or more of carboxymethyl cellulose ("CMC") high molecular weight blend, CMC low molecular weight blend, CMC moderate molecular weight blend, methylcellulose, methyl cellulose 4000, hydroxymethyl cellulose, hydroxypropyl cellulose ("HPC"), hydroxypropylmethyl cellulose high molecular weight blend ("HPMC"), hydroxyl propyl methyl cellulose 2906, carboxypropylmethyl cellulose high molecular weight blend ("CPMC"), hydroxyethyl cellulose, or hydroxyethyl cellulose and hyaluronic acid, such that the concentrations cumulatively do not create a phase transition to an in situ gel.

In preferred embodiments, the viscosity enhancer is selected from the group consisting of CMC low molecular weight blend, CMC moderate molecular weight blend, CPMC, HPC and HPMC or a combination thereof, more preferably the viscosity enhancer is HPMC and most preferably the concentration of HPMC is based on the molecular weight of Methocell® (Dow-Corning).

In other more preferred embodiments the concentration of viscosity enhancer in compositions of the present invention is from about 0.10% to about 1.75% w/v, preferably from about 0.1% to about 1.5% w/v, from about 0.5% to about 1.25% w/v, from about 0.65% to about 1.0% w/v and more preferably about 0.10% w/v, 0.20% w/v, 0.25% w/v, 0.3% w/v, 0.4% w/v, 0.5% w/v, 0.55% w/v, 0.62% w/v, 0.65% w/v, 0.75% w/v, 0.85% w/v, 1.0% w/v, 1.25% w/v, 1.3% w/v, 1.35% w/v, 1.38% w/v, 1.40% w/v, 1.45% w/v and 1.48% w/v.

Polyethylene glycol 400 ("PEG-400") is present in compositions of the present invention at concentrations from about 0.1% to about 5.0% w/v, preferably from about 0.5% to about 1.0% w/v and more preferably at about 0.5% or about 1.0% w/v Polyols suitable for use in the present invention include, but are not limited to, mannitol, glycerol, erythritol, lactitol, xylitol, sorbitol, isosorbide, and maltitol. In a more preferred embodiment, the polyol is mannitol. In another more preferred embodiment, the polyol is at a concentration from about 0.1% to about 7% w/v, from about 0.25% to about 5.5% w/v, from about 1.0% to about 4.0% w/v, from about 1.0% to about 2.5% w/v, and most preferably about 1% w/v.

Electrolytes suitable for use in the present invention include, but are not limited to, magnesium ions, sodium chloride ("NaCl"), potassium chloride ("KCl") and a combination thereof. In a more preferred embodiment, the magnesium ions are derived from magnesium chloride. In another more preferred embodiment the total electrolyte concentration in the composition is from about 0.01% to about 0.90% w/v, preferably from about 0.2% to about 0.5% w/v. In a more preferred embodiment the magnesium ions are present in the composition at a concentration from about 0.01% to about 0.25% w/v as $MgCl_2$, preferably about 0.05% to about 0.15% w/v and from about 0.075% to about 0.125% w/v, and the NaCl is present in the composition at a concentration from about 0.1% to about 0.90% w/v, preferably, from about 0.1% to about 0.75% w/v, from about 0.1% to about 0.5% w/v, and more preferably from about 0.3% to about 0.4% w/v and even more preferably about 0.4%, w/v.

In certain embodiments menthol may be used in compositions of the present invention. Preferably, menthol is at a concentration from about 0.01 to about 1.00 mM, from about 0.025 to about 0.07 mM, from about 0.07 to about 0.2 mM, from about 0.07 to about 0.1 mM, from about 0.1 to about 0.5 mM, from about 0.25 to about 0.35 mM and about 0.25, 0.3 or 0.35 mM.

In certain embodiment one or more preservatives may be used in the compositions of the present invention. Preservatives suitable for use in the present invention include, but are not limited to, benzalkonium chloride ("BAK"), sorbate, methylparaben, polypropylparaben, chlorobutanol, thimerosal, phenylmercuric acetate, perborate, phenylmercuric nitrate and combinations thereof. In a preferred embodiment, the preservative is present in the composition at a concentration from about 0.005% to about 0.2% w/v. In a more preferred embodiment BAK is present in the composition at a concentration from about 0.005% to about 0.02% w/v and sorbate is present in the composition at a concentration from about 0.015% to about 0.15% w/v.

In certain embodiment one or more antioxidants may be used in the compositions of the present invention. Antioxidants suitable for use in the present invention include, but are not limited to citrate, ethylenediaminetetraacetic acid ("EDTA") and salts thereof including disodium EDTA, sodium metabisulfite, sodium thiosulfate, acetylcysteine, butylated hydroxyanisole and butylated hydroxytoluene and a combination thereof. In a preferred embodiment, the preservative is present in the composition at a concentration from about 0.05% to about 0.2% w/v. In a more preferred embodiment EDTA is present in the composition at a concentration from about 0.05% to about 0.15% w/v.

Buffers and pH adjustors that can be used in accordance with the present invention include, but are not limited to, acetate buffers, carbonate buffers, citrate buffers, phosphate buffers and borate buffers. In a preferred embodiment, the buffers and pH adjustors are at a concentration from about 1 to about 100 millimolar. It is understood that various acids or bases can be used to adjust the pH of the composition as needed. pH adjusting agents include, but are not limited to, sodium hydroxide and hydrochloric acid. Surprisingly, pH has not been found to alter comfort in the artificial tears compositions. pH of the compositions can be from 4.0 to 8.0, more preferably from about 5.5 to about 8.0 and from about 6.0 and 7.5.

Tables 1 and 2 list preferred embodiments of the present invention. While these embodiments are meant to demonstrate preferred compositions the invention is not limited by these embodiments.

TABLE 1

Botulinum Compositions

| % w/v | #B1 | #B2 | #B3 |
|---|---|---|---|
| Botulinum toxin | 100 units | 100 units | 100 units |
| Polysorbate 80 | 3.0% | 3.0% | 3.0% |
| Poloxamer 407 | 0.2% | 0.2% | 0.2% |
| Poloxamer 188 | 1.5% | 1.5% | 1.5% |
| Polyoxyl castor oil | 0.5% | 0.5% | 0.5% |
| HPγCD | 1.5% | 1.5% | 1.5% |
| HPMC | 0.75% | 0.75% | 0.75% |
| PEG-400 | 1.0% | 1.0% | 1.0% |
| Mannitol | 1.0% | 1.0% | 1.0% |
| $MgCl_2$ | 0.1% | 0.1% | 0.1% |
| NaCl | 0.4% | 0.4% | 0.4% |
| Sorbate | 0.1% | 0.1% | 0.1% |
| Menthol | — | 0.25 mM | 0.35 mM |
| EDTA | — | — | 0.1% |
| BAK | — | — | 0.02% |
| Phosphate buffer | 3 mM | 3 mM | 3 mM |
| Water | Q.S. | Q.S. | Q.S. |

TABLE 2

Acne Compositions

| % w/v | #A1 | #A2 | #A3 | #A4 | #A5 | #A6 |
|---|---|---|---|---|---|---|
| Benzoyl peroxide | — | 2.5%-10% | 2.5%-10% | 2.5% | 5.0% | 7.5% |
| Salicylic acid | 0.5-2.0% | — | 0.5-2.0% | 0.5% | 1.0% | 1.5% |

TABLE 2-continued

Acne Compositions

| % w/v | #A1 | #A2 | #A3 | #A4 | #A5 | #A6 |
|---|---|---|---|---|---|---|
| Polysorbate 80 | 2.0% | 2.0% | 2.0% | 2.0% | 2.0% | 2.0% |
| Poloxamer 407 | 0.5% | 0.5% | 0.5% | 0.5% | 0.5% | 0.5% |
| Poloxamer 188 | 1.0% | 1.0% | 1.0% | 1.0% | 1.0% | 1.0% |
| Polyoxyl castor oil | 0.15% | 0.15% | 0.15% | 0.15% | 0.15% | 0.15% |
| HPMC | 0.75% | 0.75% | 0.75% | 0.75% | 0.75% | 0.75% |
| Sorbate | 0.11% | 0.11% | 0.11% | 0.11% | 0.11% | 0.11% |
| Menthol | 0.3 mM | 0.3 mM | 0.3 mM | 0.3 mM | 0.3 mM | 0.3 mM |
| EDTA | 0.1% | 0.1% | 0.1% | 0.1% | 0.1% | 0.1% |
| BAK | 0.02% | 0.02% | 0.02% | 0.02% | 0.02% | 0.02% |
| Benzyl alcohol | 1.0% | 1.0% | 1.0% | 1.0% | 1.0% | 1.0% |
| Glycofurol | 1.0-5.0% | 1.0-5.0% | 1.0-5.0% | 1.0-5.0% | 1.0-5.0% | 1.0-5.0% |
| Water | Q.S. | Q.S. | Q.S. | Q.S. | Q.S. | Q.S. |

EXAMPLES

Example 1—Treatment of Rhytides

Method

Facial photographs were taken of a 62-year old subject prior to and 1-day after topical application of composition #B1 to his face above the cheek and lateral to each eye.

Results

Rhytoids surrounding the lateral corners of each eye were reduced 1-day after topical application of compositions #B1. Compare A (prior) to B (subsequent) in FIG. 1.

What is claimed is:

1. A topical composition comprising botulinum toxin, polysorbate 80, poloxamer 407, poloxamer 188, polyoxyl castor oil, hydroxypropyl-gamma-cyclodextrin, hydroxypropylmethyl cellulose, mannitol, magnesium chloride, and sodium chloride.

2. The composition of claim 1, comprising:
from about 50 to about 200 units of botulinum toxin;
from about 0.5% to about 3.5% w/v polysorbate 80;
from about 0.2% to about 0.5% w/v poloxamer 407;
from about 0.1% to about 1.5% w/v poloxamer 188;
from about 0.015% to about 0.5% w/v polyoxyl castor oil;
from about 0.5% to about 5.0% w/v hydroxypropyl-gamma-cyclodextrin;
from about 0.5% to about 1.25% w/v hydroxypropylmethyl cellulose;
from about 0.5% to about 1.0% w/v polyethylene glycol 400;
from about 1.0% to about 4.0% w/v mannitol;
from about 0.075% to about 0.125% w/v magnesium chloride; and
from about 0.1% to about 0.5% w/v sodium chloride,
wherein w/v denotes weight by total volume of the composition.

3. The composition of claim 2, further comprising from about 0.1 to about 0.5 millimolar menthol.

4. The composition of claim 3, further comprising from about 0.005% to about 0.02% w/v benzalkonium chloride and from about 0.05% to about 0.15% w/v disodium ethylenediaminetetraacetic acid.

5. A topical composition comprising:
about 100 units of botulinum toxin;
about 3.0% w/v polysorbate 80;
about 0.2% w/v poloxamer 407;
about 1.5% w/v poloxamer 188;
about 0.5% w/v polyoxyl castor oil;
about 1.5% w/v hydroxypropyl-gamma-cyclodextrin;
about 0.75% w/v hydroxypropylmethyl cellulose;
about 0.5% w/v polyethylene glycol 400;
about 1.0% w/v mannitol;
about 0.1% w/v magnesium chloride; and
about 0.4% w/v sodium chloride,
wherein w/v denotes weight by total volume of the composition.

6. The composition of claim 5, further comprising from about 0.25 to about 0.35 millimolar menthol.

7. The composition of claim 6, further comprising about 0.02% w/v benzalkonium chloride and about 0.1% w/v disodium ethylenediaminetetraacetic acid.

8. A method of treating rhytides comprising topically applying the composition of claim 1 to a person in need thereof.

* * * * *